United States Patent
Syeda-Mahmood

(10) Patent No.: US 10,936,681 B2
(45) Date of Patent: Mar. 2, 2021

(54) GENERALIZED SEARCH ENGINE FOR ABSTRACT DATA TYPES WITH SKIMMING AND APPROXIMATE RETRIEVAL

(71) Applicant: INTERNATIONAL BUSINESS MACHINES CORPORATION, Armonk, NY (US)

(72) Inventor: Tanveer Syeda-Mahmood, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 48 days.

(21) Appl. No.: 15/668,472

(22) Filed: Aug. 3, 2017

(65) Prior Publication Data
US 2019/0042654 A1    Feb. 7, 2019

(51) Int. Cl.
*G06F 16/00* (2019.01)
*G06F 16/9535* (2019.01)
*G06F 16/21* (2019.01)
*G06F 16/22* (2019.01)
*G06F 16/25* (2019.01)
*G06F 19/00* (2018.01)
*G16H 50/50* (2018.01)
*G16H 50/20* (2018.01)

(52) U.S. Cl.
CPC ........ *G06F 16/9535* (2019.01); *G06F 16/213* (2019.01); *G06F 16/2228* (2019.01); *G06F 16/258* (2019.01); *G06F 19/32* (2013.01); *G16H 50/20* (2018.01); *G16H 50/50* (2018.01)

(58) Field of Classification Search
CPC .................................................. G06F 16/9535
USPC ......................................................... 707/706
See application file for complete search history.

(56) References Cited

U.S. PATENT DOCUMENTS

| | | | | |
|---|---|---|---|---|
| 5,930,800 A * | 7/1999 | Hara | ................. | G06F 16/2291 |
| 6,128,621 A * | 10/2000 | Weisz | ................. | G06F 16/258 |
| 9,378,271 B2 | 6/2016 | Rassen et al. | | |
| 2004/0236767 A1* | 11/2004 | Soylemez | ............ | G06F 16/283 |
| 2012/0130745 A1 | 5/2012 | Jones | | |
| 2013/0271777 A1* | 10/2013 | Ito | ......................... | G06F 3/1222 |
| | | | | 358/1.9 |
| 2014/0142984 A1 | 5/2014 | Wright et al. | | |
| 2015/0120695 A1* | 4/2015 | Vasu | .................... | G06F 16/182 |
| | | | | 707/711 |
| 2015/0127379 A1 | 5/2015 | Sorenson | | |
| 2019/0213407 A1 | 7/2019 | Toivanen et al. | | |
| 2020/0218738 A1 | 7/2020 | Beymer et al. | | |

* cited by examiner

*Primary Examiner* — Chelcie L Daye
(74) *Attorney, Agent, or Firm* — Erik Huestis; Stephen Kenny; Foley Hoag, LLP

(57) ABSTRACT

A generalized search engine is provided for abstract data types with skimming and approximate retrieval. According to various embodiments, an abstract data type definition is generated. The abstract data type definition comprises a plurality of field-value pairs. The abstract data type definition is indexed in an index. A document definition is generated. The document definition comprises at least one key value, and further comprises the abstract data type definition. The document definition is indexed in the index.

19 Claims, 3 Drawing Sheets

GENERALIZED SEARCH ENGINE FOR ABSTRACT DATA TYPES WITH SKIMMING AND APPROXIMATE RETRIEVAL

BACKGROUND

Embodiments of the present invention relate to search and management of abstract data types, and more specifically, to a generalized search engine for abstract data types with skimming and approximate retrieval.

BRIEF SUMMARY

According to embodiments of the present disclosure, methods of and computer program products for search and management of abstract data types are provided. In an exemplary embodiment, an abstract data type definition is generated. The abstract data type definition comprises a plurality of field-value pairs. The abstract data type definition is indexed in an index. A document definition is generated. The document definition comprises at least one key value, and further comprises the abstract data type definition. The document definition is indexed in the index.

DETAILED DESCRIPTION

A search engine framework is provided for abstract data types (ADT) in general. In various embodiments, powerful querying is possible where structured objects can be directly queried by population of relevant fields. Relative order can be preserved during querying (e.g., array order). Unlike relational schemas in databases, according to various embodiment, the ADT can be changed after design and easily updated as documents are added.

Search engine frameworks according to the present disclosure are particularly useful in field that require the storage of a variety of types of information. For example, comprehensive medical data storage may include examinations, clinical knowledge, vocabularies, and various patient data. Various exemplary embodiments described herein focus on clinical data. However, it will be appreciated that the present disclosure is useful in a variety of fields and for a variety of different data types.

According to various embodiments of the present disclosure, a uniform strategy is provided to search content by crafting documents in the index in a similar way. Common APIs are provided to Insert/update, Search, Retrieve, or Delete (soft, hard delete) content. The separation between documents and knowledge is preserved, while allowing access from one to another.

Figure 1:
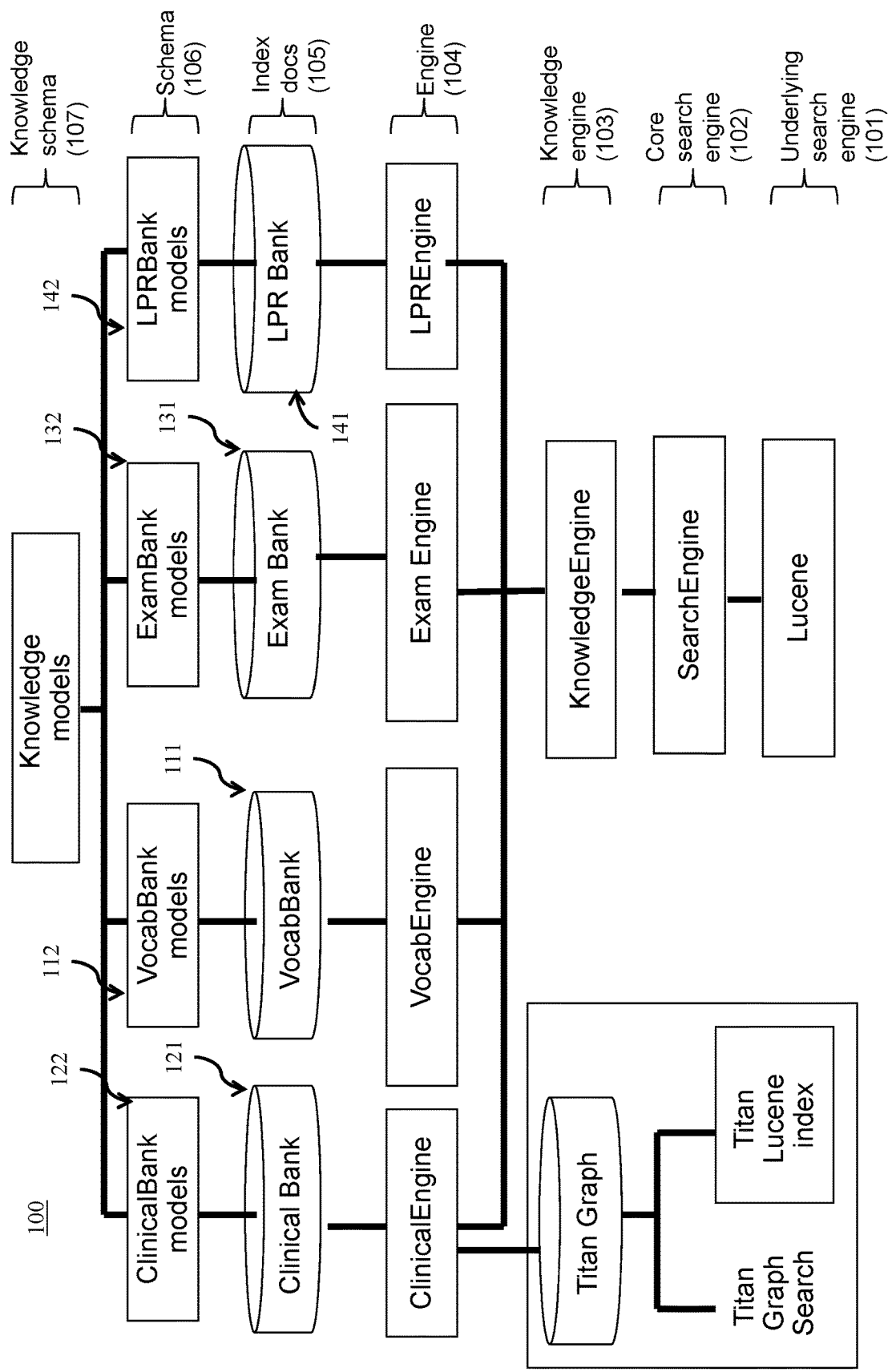
FIG. 1 illustrates a system for search and management of abstract data types according to embodiments of the present disclosure.

With reference now to FIG. 1, a system for management of abstract data types is illustrated according to embodiments of the present disclosure. In general system 100 is organized into four levels: underlying search engine 101 (which is some embodiments may be Lucene); core search engine 102; knowledge engine 103; and bank search engines 104.

Indexed documents 105 conform to corresponding schemas 106 in corresponding data models. In addition, knowledge schema 107 corresponds to an overall knowledge model. By storing and searching data models, various advantages are realized. Powerful querying is possible because structured objects can be directly queried by population of relevant fields. Relative order can be preserved during querying (e.g., array order). Unlike relational schemas in databases, the ADT can be changed after design and easily updated.

An abstract model captures essential elements needed for all data models in a given application. In the present example, the models LPRKnowledgeModel, VocabModel, ClinicalKnowledgeModel, QuestionVocabModel, ExamKnowledgeModel are domain-specific subclasses. The knowledge model captures generic elements of features derived from any knowledge objects. For example, a GenericFeature model may capture provenance, scoring, and valuetypes.

Further exploring the current example, VocabBank 111 has associated VocabBank models 112 to house different vocabulary types. The base class for VocabBank is VocabKnowledgeModel. VocabBank stores model VocabModel.

ClinicalBank 121 has associated patient-independent models. The base class for ClinicalBank is ClinicalKnowledgeModel. ClinicalBank stores six models: Category, Relation, Author, Evidence, Concept, and Assertion. Additional models are helper classes for the stored models: CategoryInfo, ConceptInfo, OntologInfo, and RelatedInfo. Context models are provided to aggregate information (not stored in ClinicalBank): Assertion, Concept, Author, Evidence, Relation, and Category.

ExamBank 131 has associated exam-specific models. The base class for ExamBank is ExamKnowledgeModel. ExamBank stores six models: AnswerChoice, ExamNew, ExamCaseNew, ExamMmItem, QuestionNew, and QuestionText. Additional models are helper classes that are not stored in the ExamBank: AChoiceType, Difficulty, MediaType, QuestionState, QuestionVocabModel, and ProgressState. Context models are provided for display (not stored in index): Exam, ExamCase, and Question.

LPRBank 141 has associated patient-specific data models. The base classes for LPR are LPRKnowledgeModel and AalimDataModel. LPRBank stores 21 models: Person, PatientDemographics, PatientAnatomy, PatientDiagnosis, PatientDrugs, PatientEncounter, PatientExamData, PatientFeature, PatientHistory, PatientInfo, PatientMeasurements, PatientMedia, PatientMediaRun, PatientOutcome, PatientRiskFactors, PatientStudy, PatientSymptoms, PatientTreatment, PatientVisit, PatientVitals, and OrgInfoModel. Additional models are helper classes for the stored models: AddressModel and ScoreModel. TOC models are stored and used to map to LPR repository structure: TOCOrg, TOCPatientExamData, TOCPatientMedia, TOCPatientMediaRun, TOCPatient, and TOCPatientStudy. Context models are provided to capture LPR repository structure for display of LPR (not stored in index): Person, PatientDemographics, PatientAnatomy, PatientDiagnosis, PatientDrugs, PatientEncounter, PatientExamData, PatientFeature, PatientHistory, PatientInfo, PatientMeasurements, PatientMedia, PatientMediaRun, PatientOutcome, PatientRiskFactors, PatientStudy, PatientSymptoms, PatientTreatment, PatientVisit, PatientVitals, and OrgInfoModel.

Each storable data model is stored as a single document. Each data model has fields ($f_1, f_2, \ldots f_n$). Each data model can have primary keys, search keys, grouping keys, and untokenized keys. Primary keys are similar to primary key in a relational table, for example, providing a unique ID or set of IDs to designate a row or a document uniquely. Search keys are similar to logical primary keys in a relational table. Grouping keys are used for skimming in search. In some embodiments, Lucene keeps track of them through special collectors. Untokenized keys tell the lowest level search engine document formation step to preserve certain fields without tokenization. This field is useful for enumerated types. In various embodiments, the above information is stored as Java annotations.

The ADT representation in a document is as follows. The original data model may be represented as a set of name-value pairs ADT={<$f_1, v_1,$ >, <$f_2, v_2$>, ... <$f_n, v_n$>}. Only one copy of the same name-value pair is indexed. A created document may be represented as D=<$F_g, F_p, F_u, F_i,$ m,u, S>.

A grouping key may be represented as $F_g=\{<f_g, v_g>\}$, $|F_g|=1$. An untokenized key may be represented as $F_u=\{<f_u, v_u>, f_u.fsn, v_u\}$, $|F_u|\geq 0$. A primary key may be represented as $F_p=\{<f_p.ORG, v_p>\}, |F_p|\geq 1$.

$F_i=\{H_i\}, |F_i|\geq 1$, where $$H_i = \begin{cases} K(f_i) \text{ if } f_i \text{ is atomic} \\ <\{K(l_j)\}, <f_i \cdot \text{length}, |f_i| >> \forall\ l_j \in f_i, \end{cases}$$

if $f_i$ is an array and $K(f_i)=\{K^o(f_i), K^{fsn}(f_i), K^{fieldname}(f_i), K^t(f_i), K^n(f_i), K^d(f_i)\}$. Given the original field-value pairs, $K^o(f_i)=$ <$f_i, v_i,$ >. Normalized value may be represented as $K^{fsn}(f_i)=$<$f_i.fsn, N(v_i)$>, $N(v_i)$. Tokenized value may be represented as $K^t(f_i)=\{<f_i, v_{ti}>\}, v_{ti}$ is a term of $v_i$. For fieldname="field-value", $K^{fieldname}(f_i)=$<fieldname, "$f_i=v_i$">. For number terms as numeric fields, $K^n(f_i)=\{<f_i, v_{ni}>\}, v_{ni}$ is a numeric term of $v_i$. For date terms as date fields, $K^d(f_i)=\{<f_i, v_{di}>\}$, $v_{di}$ is a date term of $v_i$.

m=<modelname=Name(ADT)>.

$$u = <\text{Name}(ADT) \cdot \text{updateStatus} = \begin{cases} \text{NO\_DELETE} \\ \text{SOFT\_DELETE} \\ \text{HARD\_DELETE} \end{cases}.$$

S=<serialized_obj=Serialized(ADT)>.

Adopting the above example, consider the multiple field types provided below in Inset 1.

---
Inset 1
---
ConceptModel.name ="Hello World"
ConceptModel.score=2.0
ConceptModel.date="10-21-2014"
ConceptModel.ontology[0].conceptname="Foo Baz 223 10-22-2014"

---

The field value pairs indexed are then provided in Inset 2-Inset 5.

---
Inset 2
---
ConceptModel.name="Hello  World"
ConceptModel.name.fsn="hello world"
fieldname="ConceptModel.name=Hello World"

---
Inset 2
---
ConceptModel.name="hello"
ConceptModel.name="world"

---
Inset 3
---
ConceptModel.score=2.0
ConceptModel.score.fsn=2.0
fieldname="ConceptModel.score=2.0"
ConceptModel.score="2.0"

---
Inset 4
---
ConceptModel.date="10-21-2014"
ConceptModel.date.fsn="10-21-2014"
fieldname="ConceptModel.date=10-21-2014"
ConceptModel.date="20141021093211"

---
Inset 5
---
Fieldname="ConceptModel.ontology.length=1"
ConceptModel.ontology.conceptname="Foo Baz 223 10-22-2014"
ConceptModel.ontology.conceptname.fsn="foo baz 223 10-22-2014"
fieldname="ConceptModel.ontology.conceptname="Foo Baz 10-22-2014"
ConceptModel.ontology.conceptname="foo"
ConceptModel.ontology.conceptname="baz"
ConceptModel.ontology.conceptname="223"
ConceptModel.ontology.conceptname=223.0
ConceptModel.ontology.conceptname="10-22-2014"
Conceptmodel.ontology.conceptname="20141022093224"

---

As noted above, various operation on documents are provided according to embodiments of this disclosure. These may include inserts, updates, deletes, search, skim, sharding, and batch operations.

Considering index operations on a single index, including inserts, updates, and deletes, the input is a data model derived from KnowledgeModel. The output is a new document corresponding to the data model in the index. To check if a document already exists in the index, the search keys or the primary key may be used if a specific document is desired. Retrieving the existing document may include a HARD_DELETE, deleting the document from the index, a SOFT_DELETE updating the retrieved model with a status of SOFT_DELETE, or UPDATE, merging the current model with the retrieved model.

Adding a new document may include extract all fields of the knowledge model, including inherited fields, creating an initial document with the fields, enhancing the document, drop the document from the index if it exists, and insert the new document.

Search operations on a single index may include various options. For example, search options may be based on input types, including Boolean Queries (when one wants to be specific and knows field names) or Partially filled data models. In some embodiments, automatic query expansion is provided by tokenization of fields. Various search methods are provided, including skimming (counting how many matches are there), generic search (searching for unknown models=>multiple models returned), and retrieve (searching for known model=>resulting model is unique). Various desired outputs are available, including fully populated data models, documents grouped by search keys (more details on documents, allows for re-ranking post-search), and ranked document ID lists (for quick pruning). In some embodiments, each document has a Lucene score and numhits for separate scoring.

In various embodiments, query expansion is provided. When queries are partial data models, all active fields are extracted (e.g., non-null or non-initialized). Each field type is inspected and an appropriate boolean query is formulated. Strings get tokenized, phrase-ordered with slop in addition to their original form. Numbers get formulated as both strings, and numeric query ranges. Dates get formulated as strings and dates in both time formats (UTC and string form). UUID and other untokenized types are retained as is. In various embodiments, further customization is provided in respective bank search engines. For example, synonym expansion or ontological expansion may be provided for the exemplary ClincalBank.

When indexes grow larger than about 100 GB, custom sharding may be necessary. In various embodiments, all data about a given entity is located in the same shard (e.g., for a given patient). Batch inserts and deletes are desirable in various implementations, which requires grouping all documents belonging to a single shard. In addition, various embodiments provide parallel search of shards through independent index searchers.

For batch insert, update, or deletes with sharding, the input is a list of data models to be inserted, updated, or deleted. The output is updated documents in the index. For each model, the shard it belongs to and its size are identified. A Boolean query may be created for the model. All models with hits are grouped in their respective shards and updated models are retrieved after merging and enhancing. A large Boolean query is formed per shard of all the models in the shard. The old documents are batch deleted. The new documents are batch inserted.

To provide search with sharding, all searchers for index shardsare collected. Matching shards are found per query. Shards are searched separately (which can be parallelized). The results returned are merged.

It will be appreciated that the system described above is useful in a variety of environments for a variety of data types. For example, all organizations in the LPRBank can be found by making an empty OrgInfoModel and passing it to generic search. In another example, all concepts which are ontologically related by two levels of depth in between can be found by constructing a ConceptModel with an ontology element of distance=2.

Figure 2:
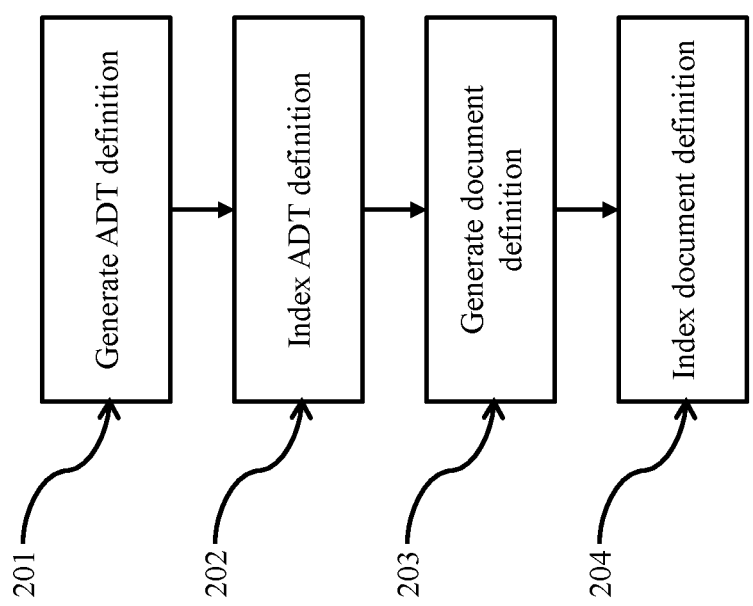
FIG. 2 illustrates a method for search and management of abstract data types according to embodiments of the present disclosure.

Referring now to FIG. 2, a method for search and management of abstract data types is illustrated according to embodiments of the present disclosure. At 201, an abstract data type definition is generated. The abstract data type definition comprises a plurality of field-value pairs. At 202, the abstract data type definition is indexed in an index. At 203, a document definition is generated. The document definition comprises at least one key value, and further comprises the abstract data type definition. At 204, the document definition is indexed in the index.

Figure 3:
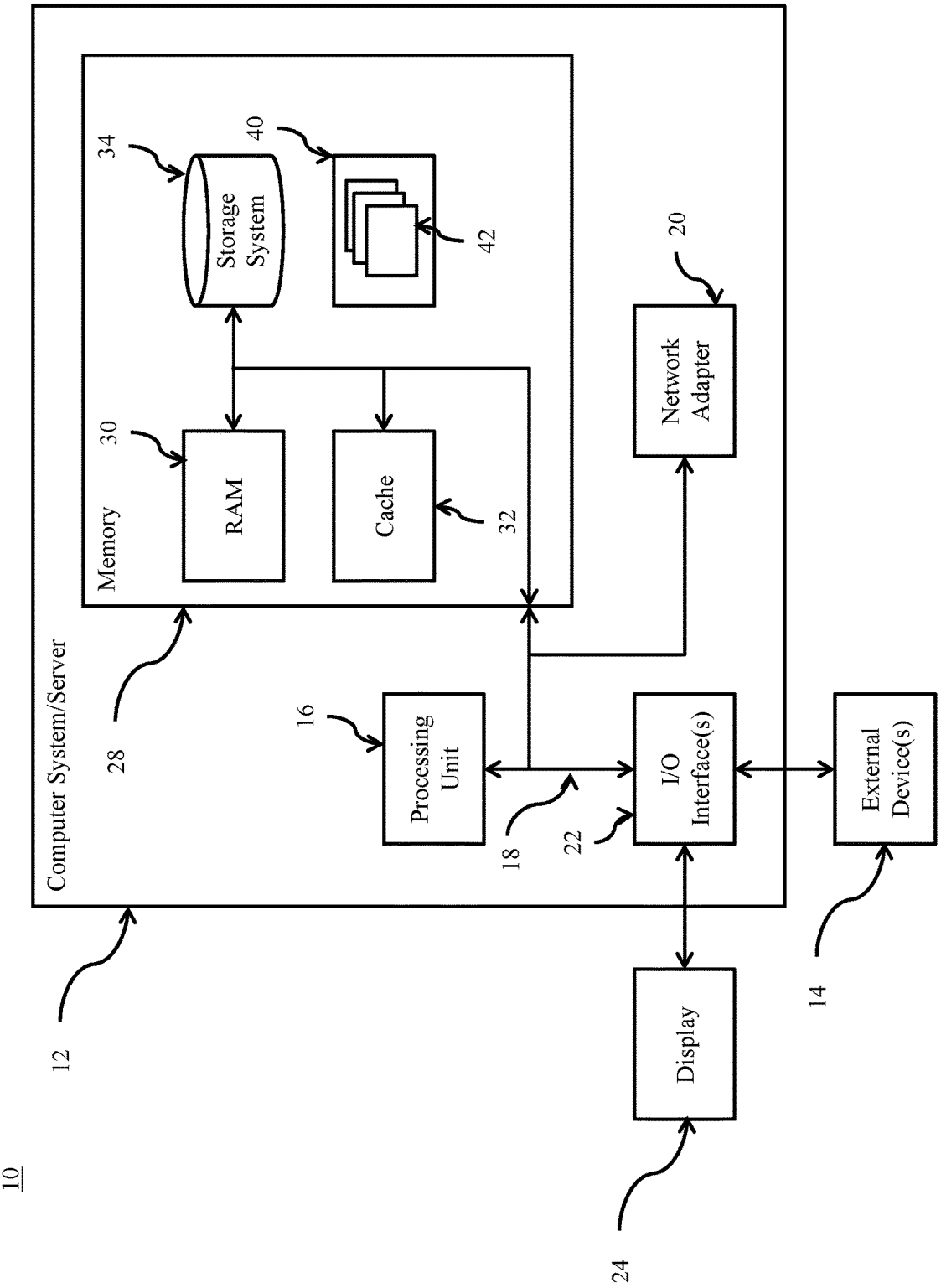
FIG. 3 depicts a computing node according to embodiments of the present disclosure.

Referring now to FIG. 3, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 3, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
    generating an abstract data type definition, the abstract data type definition comprising a plurality of field-value pairs;
    indexing the abstract data type definition in an index;
    generating a document definition, the document definition comprising at least one key value, and further comprising the abstract data type definition, the at least one key value identifying the document definition and comprising a primary key configured to uniquely designate a row or a document, a search key configured to separately designate a row or a document, a grouping key configured to count number of matches to a query, and an untokenized key configured to preserve one or more predetermined fields of the document definition without tokenization;
    indexing the document definition in the index.

2. The method of claim 1, wherein the document definition comprises a serialized form of the abstract data type definition.

3. The method of claim 1, further comprising:
    modifying the abstract data type.

4. The method of claim 1, further comprising:
    performing an insert, update, or delete on the index.

5. The method of claim 1, wherein the index comprises a Lucene index.

6. The method of claim 1, further comprising:
    searching the index for a plurality of abstract data types.

7. The method of claim 1, further comprising:
    sharding the index such that documents in the index are allocated based on an associated entity.

8. A system comprising:
    a data store comprising an index;
    a computing node comprising a computer readable storage medium having program instructions embodied therewith, the program instructions executable by a processor of the computing node to cause the processor to perform a method comprising:
        generating an abstract data type definition, the abstract data type definition comprising a plurality of field-value pairs;
        indexing the abstract data type definition in an index;
        generating a document definition, the document definition comprising at least one key value, and further comprising the abstract data type definition, the at least one key value identifying the document definition and comprising a primary key configured to uniquely designate a row or a document, a search key configured to separately designate a row or a document, a grouping key configured to count number of matches to a query, and an untokenized key configured to preserve one or more predetermined fields of the document definition without tokenization;
        indexing the document definition in the index.

9. A computer program product for search and management of abstract data types, the computer program product comprising a computer readable storage medium having program instructions embodied therewith, the program instructions executable by a processor to cause the processor to perform a method comprising:
    generating an abstract data type definition, the abstract data type definition comprising a plurality of field-value pairs;
    indexing the abstract data type definition in an index;
    generating a document definition, the document definition comprising at least one key value, and further comprising the abstract data type definition, the at least one key value identifying the document definition and comprising a primary key configured to uniquely designate a row or a document, a search key configured to separately designate a row or a document, a grouping key configured to count number of matches to a query, and an untokenized key configured to preserve one or more predetermined fields of the document definition without tokenization;
    indexing the document definition in the index.

10. The computer program product of claim 9, wherein the document definition comprises a serialized form of the abstract data type definition.

11. The computer program product of claim 9, further comprising:
    modifying the abstract data type.

12. The computer program product of claim 9, further comprising:
    performing an insert, update, or delete on the index.

13. The computer program product of claim 9, wherein the index comprises a Lucene index.

14. The computer program product of claim 9, further comprising:
    searching the index for a plurality of abstract data types.

15. The computer program product of claim 9, further comprising:
    sharding the index such that documents in the index are allocated based on an associated entity.

16. The method of claim 1, wherein duplicate field-value pairs in the plurality of field-value pairs are not indexed.

17. The computer program product of claim 9, wherein duplicate field-value pairs in the plurality of field-value pairs are not indexed.

18. The method of claim 2, wherein the document definition further comprises a model name and an update status of the abstract data type definition.

19. The computer program product of claim 10, wherein the document definition further comprises a model name and an update status of the abstract data type definition.

\* \* \* \* \*